United States Patent
Kanaya

(10) Patent No.: US 9,969,678 B2
(45) Date of Patent: May 15, 2018

(54) METHOD OF PRODUCING OPTICALLY ACTIVE β-AMINOCARBONYL COMPOUND

(71) Applicant: DEXERIALS CORPORATION, Tokyo (JP)

(72) Inventor: Hiroki Kanaya, Utsunomiya (JP)

(73) Assignee: DEXERIALS CORPORATION, Tokyo (JP)

( * ) Notice: Subject to any disclaimer, the term of this patent is extended or adjusted under 35 U.S.C. 154(b) by 0 days. days.

(21) Appl. No.: 14/939,571

(22) Filed: Nov. 12, 2015

(65) Prior Publication Data

US 2016/0159729 A1 Jun. 9, 2016

(30) Foreign Application Priority Data

Dec. 3, 2014 (JP) .................................. 2014-245036

(51) Int. Cl.
*C07C 221/00* (2006.01)

(52) U.S. Cl.
CPC ........ *C07C 221/00* (2013.01); *C07B 2200/07* (2013.01); *C07C 2101/14* (2013.01); *C07C 2101/18* (2013.01)

(58) Field of Classification Search
None
See application file for complete search history.

(56) References Cited

FOREIGN PATENT DOCUMENTS

| JP | 2975943 B2 | 11/1999 |
| JP | 2981547 B1 | 11/1999 |
| JP | 3616909 B2 | 2/2005 |
| JP | 4741199 B2 | 8/2011 |

OTHER PUBLICATIONS

Kristensen et al., "Synthesis of Acrylic Polymer Beads for Solid-Supported Proline-Derived Organocatalysts," Organic Letters, 2009, vol. 11, No. 14, pp. 2968-2971.
Kristensen et al., "A General Approach for Preparation of Polymer-Supported Chiral Organocatalysts via Acrylic Copolymerization," J. Org. Chem., 2010, vol. 75, pp. 1620-1629.
Gruttadauria et al., "Hydrophobically Directed Aldol Reactions: Polystyrene-Supported L-Proline as a Recyclable Catalyst for Direct Asymmetric Adol Reactions in the Presence of Water," Eur. J. Org. Chem., 2007, pp. 4688-4698.
Kristensen et al., Supporting Information for "Synthesis of Acrylic Polymer Beads for Solid-Supported Proline-Derived Organocatalysts," Part I, pp. 1-12.

*Primary Examiner* — Clinton A Brooks
(74) *Attorney, Agent, or Firm* — Oliff PLC

(57) ABSTRACT

In a method of producing an optically active β-aminocarbonyl compound using a column reactor, a column for a column reactor is charged with asymmetric catalyst particles to form a column reactor. Compounds for a Mannich-type reaction are introduced into the column reactor to be brought into contact with the asymmetric catalyst particles, to thereby convert the compounds to an optically active β-aminocarbonyl compound. The preferable asymmetric catalyst particles are resin particles that are prepared from a monomer composition containing a proline derivative monomer having an unsaturated bond and a radical polymerization initiator, and that act as a catalyst for an asymmetric Mannich-type reaction.

22 Claims, No Drawings

METHOD OF PRODUCING OPTICALLY ACTIVE β-AMINOCARBONYL COMPOUND

BACKGROUND OF THE INVENTION

1. Field of the Invention

The present invention relates to a method of producing an optically active β-aminocarbonyl compound by an asymmetric Mannich-type reaction using a column reactor.

2. Description of the Related Art

A proline and a derivative thereof have been found to act as an organocatalyst in an organic synthesis. In particular, the proline and derivative thereof have advantages in which an optically active proline skeleton can be easily obtained, a metal is not used, and a usage environment is not limited. It has been known that an optically active syn-β-aminocarbonyl compound is obtained at high yield with high enantioselectivity by a catalytic activity of such a proline in a homogeneous liquid-phase Mannich-type reaction effective for the synthesis of a pharmaceutical raw material, or the like (Patent Literature 1). However, in the homogeneous liquid-phase Mannich-type reaction, it is difficult that the proline derivative as the catalyst is removed from the reaction mixture at low cost. For this reason, the formation of a solid-phase catalyst from the proline derivative has been proposed. For example, the following technique has been proposed (Non-Patent Literature 1). A monomer composition containing an acrylate derivative monomer having a proline structure in the molecule, an unsaturated compound such as styrene and divinylbenzene, and a radical polymerization initiator is subjected to suspension polymerization, to obtain resin particles. A solution of carbonyl compound having an α-hydrogen is placed in a reaction vessel, and the resin particles as asymmetric solid-phase catalyst particles are added thereto. The reaction mixture is heated under uniform mixing to obtain an aldol reaction product through a batch process. It is considered that this technique is applied to an asymmetric Mannich-type reaction.

CITATION LIST

Patent Literature 1: Japanese Patent No. 4741199
Non-Patent Literature 1: ORGANIC LETTERS, 2009, vol. 11, No. 14, pp. 2968-2971

SUMMARY OF THE INVENTION

Problem(s) to be Solved by the Invention

However, the asymmetric Mannich-type reaction using the asymmetric catalyst particles through a batch process, as described in Non-Patent Literature 1, has problems in which a stirring rate, a reaction time, a reaction temperature, and the like need to be separately controlled. There is a further problem in which a complex separation operation is required during separation of the reaction product from the catalyst.

In order to solve the problems in the conventional techniques, it is an object of the present invention to provide a method of producing an optically active β-aminocarbonyl compound using asymmetric catalyst particles as a solid-phase catalyst so that an organic synthesis based on an asymmetric Mannich-type reaction can be easily performed without considering the reaction scale and a reaction product can be separated from the catalyst without a complex separation operation.

Means for Solving the Problems

The present inventors have found that the object of the present invention is achieved by preparing a column reactor in which a column is charged with asymmetric catalyst particles, and introducing compounds for a Mannich-type reaction into the column reactor to bring the compounds into contact with the asymmetric catalyst particles, to thereby convert the compounds for a Mannich-type reaction to an optically active β-aminocarbonyl compound. As a result, the present invention has been completed.

First Aspect

Specifically, the present invention provides a method of producing an optically active β-aminocarbonyl compound by an asymmetric Mannich-type reaction using a column reactor in which a column is charged with asymmetric catalyst particles, wherein the asymmetric catalyst particles are resin particles prepared from a monomer composition containing a monomer having an asymmetric source, and the method includes introducing compounds for a Mannich-type reaction into the column reactor to bring the compounds into contact with the asymmetric catalyst particles, to thereby convert the compounds for a Mannich-type reaction to an optically active β-aminocarbonyl compound.

Second Aspect

The present invention provides a column reactor in which a column for a column reactor is charged with asymmetric catalyst particles, wherein the asymmetric catalyst particles are resin particles that are prepared from a monomer composition containing a proline derivative monomer having an unsaturated bond and a radical polymerization initiator and act as a catalyst for an asymmetric Mannich-type reaction.

Third Aspect

The present invention provides a method of producing a column reactor, including charging a column for a column reactor with asymmetric catalyst particles, wherein the asymmetric catalyst particles are resin particles that are prepared from a monomer composition containing a proline derivative monomer having an unsaturated bond and a radical polymerization initiator and act as a catalyst for an asymmetric Mannich-type reaction.

Hereinafter, typical modifications of the first to third aspects will be described.

Modification 1 of First Aspect

A modification 1 of the first aspect is a method of producing an optically active β-aminocarbonyl compound by an asymmetric Mannich-type reaction using a column reactor in which a column is charged with asymmetric catalyst particles, the method including introducing compounds for a Mannich-type reaction into the column reactor to bring the compounds into contact with the asymmetric catalyst particles, to thereby convert the compounds for a Mannich-type reaction to an optically active β-aminocarbonyl compound, wherein the asymmetric catalyst particles are resin particles that are prepared from a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a monomer having an asymmetric source, and a radical polymerization initiator, and act as a catalyst for the asymmetric Mannich-type reaction.

Modification 2 of First Aspect

A modification 2 of the first aspect is a method of producing an optically active β-aminocarbonyl compound by an asymmetric Mannich-type reaction using a column reactor in which a column is charged with asymmetric catalyst particles, the method including introducing p-anisidine, dimethoxyacetaldehyde, and cyclohexanone into the column reactor to bring them into contact with the asymmetric catalyst particles, to thereby obtain (1'S,2S),2-(2',2'-dimethoxy-1'-(4"-methoxyphenylamino)ethyl)cyclohexanone as an optically active β-aminocarbonyl compound, wherein the asymmetric catalyst particles are resin particles that are prepared from a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a monomer having an asymmetric source, and a radical polymerization initiator, and act as a catalyst for the asymmetric Mannich-type reaction.

Modification 3 of First Aspect

A modification 3 of the first aspect is a method of producing an optically active β-aminocarbonyl compound by an asymmetric Mannich-type reaction using a column reactor in which a column is charged with asymmetric catalyst particles, the method including introducing p-anisidine, dimethoxyacetaldehyde, and cyclohexanone into the column reactor to bring them into contact with the asymmetric catalyst particles to thereby obtain (1'S,2S),2-(2',2'-dimethoxy-1'-(4"-methoxyphenylamino)ethyl)cyclohexanone as an optically active β-aminocarbonyl compound, and further performing optical resolution in the column reactor, wherein the asymmetric catalyst particles are resin particles that are prepared from a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a monomer having an asymmetric source, and a radical polymerization initiator, and act as a catalyst for the asymmetric Mannich-type reaction.

Modification 4 of First Aspect

A modification 4 of the first aspect is a method of producing an optically active β-aminocarbonyl compound by an asymmetric Mannich-type reaction using a column reactor in which a column is charged with asymmetric catalyst particles, the method including introducing p-anisidine, dimethoxyacetaldehyde, and cyclohexanone into the column reactor to bring them into contact with the asymmetric catalyst particles to thereby obtain (1'S,2S),2-(2',2'-dimethoxy-1'-(4"-methoxyphenylamino)ethyl)cyclohexanone as an optically active β-aminocarbonyl compound, and further performing optical resolution in the column reactor, wherein the asymmetric catalyst particles are resin particles that are prepared through a microchannel method in which a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a monomer having an asymmetric source, and a radical polymerization initiator is discharged into a continuous phase to form droplets of the monomer composition in the continuous phase, and the droplets are heated to radically polymerize the proline derivative monomer having an unsaturated bond, and act as a catalyst for the asymmetric Mannich-type reaction.

Modification 1 of Second Aspect

A modification 1 of the second aspect is a column reactor in which a column for a column reactor is charged with asymmetric catalyst particles, wherein the asymmetric catalyst particles are resin particles that are prepared by discharging a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a proline derivative monomer having an unsaturated bond, and a radical polymerization initiator into a continuous phase to form droplets of the monomer composition in the continuous phase, and heating the droplets to radically polymerize the proline derivative monomer having an unsaturated bond, and act as a catalyst for the asymmetric Mannich-type reaction.

Modification 1 of Third Aspect

A modification 1 of the third aspect is a method of producing a column reactor, including charging a column for a column reactor with asymmetric catalyst particles, wherein the asymmetric catalyst particles are resin particles that are prepared by discharging a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a proline derivative monomer having an unsaturated bond, and a radical polymerization initiator into a continuous phase to form droplets of the monomer composition in the continuous phase, and heating the droplets to radically polymerize the proline derivative monomer having an unsaturated bond, and act as a catalyst for the asymmetric Mannich-type reaction.

Advantageous Effects of the Invention

According to the method of producing an optically active β-aminocarbonyl compound, compounds for a Mannich-type reaction are introduced into a column reactor that is charged with asymmetric catalyst particles as a solid-phase catalyst to be brought into contact with the asymmetric catalyst particles, to thereby convert the compounds to an optically active β-aminocarbonyl compound. Therefore, an organic synthesis based on an asymmetric Mannich-type reaction can be easily performed without considering the reaction scale and the optically active β-aminocarbonyl compound can be separated from the asymmetric catalyst particles without a complex separating operation.

DETAILED DESCRIPTION OF THE INVENTION

A method of producing an optically active β-aminocarbonyl compound by an asymmetric Mannich-type reaction using a column reactor according to the present invention includes the following steps (a) and (b). Hereinafter, each step will be described.

<Step (a)>

A column for a column reactor is charged with asymmetric catalyst particles, described below, to form a column reactor. Examples of the column for a column reactor may include a glass column, a ceramic column formed from alumina, etc., and a metal column formed from stainless, etc. A column for HPLC may also be used. The column is generally provided with an inlet for introducing a reaction liquid on one end and an outlet for discharging the reaction liquid on the other end.

From the viewpoints of handleability and the effects of the present invention, the column generally has a size of 4.6 to 200 mm in inner diameter and 10 to 10,000 mm in length.

The column may be charged with the asymmetric catalyst particles through a known charging procedure. From the viewpoints of the effects of the present invention, the column is charged with a dispersion obtained by dispersing the asymmetric catalyst particles in a solvent such as ethanol at a flow rate of 0.1 to 500 mL/min and a pressure of up to 10 to 200 MPa.

A decrease in the particle diameter of the asymmetric catalyst particles increases the surface area per unit mass of the asymmetric catalyst particles, and as a result, a reaction field increases. Therefore, the frequency of contact of compounds for a reaction with the asymmetric catalyst particles increases. In contrast, an increase in the particle diameter facilitates injection of liquid into the column reactor. Accordingly, the particle diameter measured by a flow-type particle image analysis method is preferably 0.5 to 50 µm, and more preferably 1 to 10 µm.

<Step (b)>

Subsequently, compounds for a Mannich-type reaction are introduced into the column reactor to be brought into contact with the asymmetric catalyst particles, to thereby convert the compounds to an optically active β-aminocarbonyl compound. In this case, the column reactor may be injected with a reaction solution in which the compounds for a Mannich-type reaction are dissolved in a solvent (for example, hexane) by a conventional method, for example, using a system for HPLC. The solvent used in the injection may be appropriately selected according to the kinds and the like of the compounds for a Mannich-type reaction. From the viewpoints of the effects of the present invention, hexane or the like can be used. It is preferable that the pressure be 10 to 200 MPa, the flow rate be 0.1 to 500 mL/min, and the injection time be 0.5 to 250 hours.

The produced optically active β-aminocarbonyl compound is extruded with the solvent from the outlet of the column reactor. Therefore, it is desirable that a volume and a time for separation be determined. If necessary, the separated portion containing the optically active β-aminocarbonyl compound is concentrated, and the concentrate is analyzed for determining the reaction ratio of the optically active β-aminocarbonyl compound by HPLC from the viewpoints of effects of the present invention. The HPLC conditions are that the used solvent is a mixed solvent of hexane and isopropyl alcohol (99.9:0.1 to 70:30 (% by volume)), and the flow rate is 0.1 to 5 mL/min. From the analysis results, the method of producing an optically active β-aminocarbonyl compound according to the present invention makes it possible that the enantiomeric excess is preferably 50 to 100% e.e. or more.

As the compounds for a Mannich-type reaction, three components including a primary or secondary amine compound, a carbonyl compound having no α-hydrogen or a carbonyl compound that equivalently causes a Mannich-type reaction, and a compound having an active α-hydrogen are selected. The carbonyl compound having no α-hydrogen (or the carbonyl compound that equivalently causes a Mannich-type reaction) is an aldehyde compound that may react with the primary or secondary amine compound to produce an imine compound or an iminium cation compound. The compound having an active α-hydrogen is a carbonyl compound that may be converted into an enol compound that reacts with the imine compound or the iminium cation compound.

Specifically, the compounds for a Mannich-type reaction include an amine compound represented by the formula (1), an aldehyde compound that reacts with the amine compound to produce an imine compound or an iminium cation compound and is represented by the formula (2), and a carbonyl compound having an α-hydrogen that may be converted into an enol compound that reacts with the imine compound or the iminium cation compound and is represented by the formula (3).

In the column reactor, the amine compound of the formula (1) reacts with the aldehyde compound of the formula (2) to produce an imine compound or an iminium cation compound. The carbonyl compound of the formula (3) is enolized, and reacts with the imine compound or the iminium cation compound in the presence of the asymmetric catalyst particles, to thereby obtain the optically active β-aminocarbonyl compound. In this case, the carbonyl compound having an α-hydrogen of the formula (3) is dissolved with an organic base such as triethyl amine that acts as a promotor of the Mannich-type reaction in a solvent such as hexane, if necessary, and this solution (mobile phase) is introduced into the column reactor. Therefore, it is preferable that a solvent in the column reactor be replaced with the solvent used during introduction of the asymmetric catalyst particles in the column reactor in advance. After the replacement, it is preferable that a mixture liquid including the amine compound of the formula (1) and the aldehyde compound of the formula (2) be introduced into the column reactor.

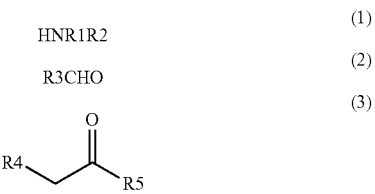

In the formula, R1, R2, and R3 are each independently a hydrogen atom, an aryl group, an aroyl group, a hetero-ring group, an alkyl group, an alkenyl group, or an alkynyl group, provided that R1 and R2 are not simultaneously hydrogen atoms. R4 and R5 are each independently a hydrogen atom, an alkyl group, an alkenyl group, or an alkynyl group. R4 and R5 may be bonded together to form a ring.

Examples of the aryl group in R1, R2, and R3 may include a phenyl group, a naphthyl group, and a fluorene group. Examples of the aroyl group may include a benzoyl group, a toluoyl group, a cinnamoyl group, a naphthoyl group, and a pyridylcarbonyl group. Examples of the hetero-ring group may include a piperidinyl group, a furanyl group, a thiophenyl group, a pyrrolyl group, a pyrazolyl group, an imidazolyl group, a triazolyl group, an oxazolyl group, an isoxazolyl group, a thiazolyl group, an isothiazolyl group, a dioxolanyl group, a pyridinyl group, a pyrimidinyl group, a pyrazinyl group, a triazinyl group, a dioxanyl group, a dithianyl group, a morpholinyl group, an azepinyl group, an oxepinyl group, and a thiepinyl group. These aryl, aroyl, and hetero-ring groups may further have a substituent. Examples of the substituent may include an alkyl group, an alkenyl group or an alkynyl group, a nitro group, a halogen atom (for example, fluorine atom, chlorine atom, bromine atom, and iodine atom), an alkyoxyl group, and an alkenyloxy group.

The alkyl group in R1, R2, R3, R4, and R5 is an alkyl group having 1 to 20 carbon atoms, and preferably 1 to 6 carbon atoms. Examples thereof may include a methyl group, an ethyl group, a propyl group, an isopropyl group, a n-butyl group, a sec-butyl group, a tert-butyl group, a pentyl group, a hexyl group, a heptyl group, a n-octyl group, a 2-ethylhexyl group, a tert-octyl group, a nonyl group, a decyl group, a dodecyl group, a tridecyl group, a tetradecyl group, a pentadecyl group, a n-hexadecyl group, a 2-hexyldecyl group, a heptadecyl group, an octadecyl group, a nonadecyl group, and an icosyl group. The alkenyl group is an alkenyl group having 2 to 20 carbon atoms, and preferably 2 to 6 carbon atoms. Examples thereof may include a propenyl group such as a vinyl group and an allyl group, a butyryl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, and an icocenyl group. These groups may be a terminal olefin or an internal olefin. The alkynyl group is an alkynyl group having 2 to 20 carbon atoms, and preferably 2 to 6 carbon atoms. Examples thereof may include an ethynyl group, a propynyl group, a butynyl group, a pentynyl group, a hexynyl group, a heptynyl group, an octynyl group, a nonynyl group, a decynyl group, an undecynyl group, a dodecynyl group, a tridecynyl group, a tetradecynyl group, a pentadecynyl group, a hexadecynyl group, a heptadecynyl group, an octadecynyl group, a nonadecynyl group, and an icosynyl group. These groups may be a terminal alkyne or an internal alkyne. These alkyl, alkenyl, and alkynyl groups may further have a substituent. Examples of the substituent may include the aryl groups, the aroyl groups, and the hetero-ring groups described above. These groups may be substituted with an alkyl group, an alkenyl group or an alkynyl group, a nitro group, a halogen atom (for example, fluorine atom, chlorine atom, bromine atom, and iodine atom), an alkyoxyl group (for example, an alkoxy group having 1 to 6 carbon atoms such as a methoxy group, an ethoxy group, a propoxy group, a butoxy group, a pentyloxy group, and a hexyloxy group), or an alkenyloxy group (for example, an alkenyloxy group having 2 to 6 carbon atoms such as a vinyloxy group, an allyloxy group, a butenyloxy group, a pentenyloxy group, and a hexenyloxy group).

Examples of the ring formed by bonding R4 and R5 may include cycloalkanone (for example, cyclobutanone, cyclopentanone, cyclohexanone, and cycloheptanone), cycloalkenone (for example, butenone, cyclopentenone, cyclohexenone, and cycloheptenone), and cycloalkynone (for example, cyclhexynone, and cycloheptynone). Among them, cyclohexanone is preferred.

The aldehyde compound of the formula (2) and the carbonyl compound having an α-hydrogen of the formula (3) may be the same. From the viewpoints of increase in the yield of a target compound, it is preferable that the compounds be different.

Examples of the amine compound of the formula (1) may include a monoalkylamine such as hexylamine, a dialkylamine such as dihexylamine, a monoarylamine such as phenylamine, and a diarylamine such as diphenylamine. Among them, a monoarylamine is preferred from the viewpoints of increase in the yield of the target compound. In particular, a monophenylamine derivative (aniline derivative) is preferred. Specific examples of the aniline derivative may include anisidine, chloroaniline, bromoaniline, iodoaniline, aniline, dimethoxyaniline, and trimethoxyaniline. In particular, p-anisidine is preferred from the viewpoints of reactivity and increase in the yield of the target compound.

Examples of the aldehyde compound of the formula (2) may include acyclic aldehydes such as formaldehyde, acetaldehyde, dimethoxyacetaldehyde, propanal, butyral, pentanal (valeraldehyde), and hexanal, alicyclic aldehydes such as cyclohexyl carboaldehyde, and aromatic aldehydes such as benzaldehyde, 4-nitrobenzaldehyde, 3-nitrobenzaldehyde, and 4-trifluoromethyl benzaldehyde. Among them, dimethoxyacetaldehyde is preferred from the viewpoints of general purpose and increase in the yield of the target compound.

Examples of the carbonyl compound having an α-hydrogen of the formula (3) may include acyclic aldehydes such as acetaldehyde, dimethoxyacetaldehyde, propanal, butyral, pentanal (valeraldehyde), and hexanal, alicyclic aldehydes such as cyclohexyl carboaldehyde, acyclic ketones such as acetone, methyl ethyl ketone, and diethyl ketone, and cyclic ketones such as cyclobutanone, cyclobutenone, cyclopentanone, cyclopentenone, cyclohexanone, and cyclohexenone. Among them, cyclohexanone is preferred from the viewpoints of increase in the yield of the target compound.

Therefore, a particularly preferred combination of the compounds for a Mannich-type reaction is a combination of p-anisidine as the amine compound of the formula (1), dimethoxyacetaldehyd as the aldehyde compound of the formula (2), and cyclohexanone as the carbonyl compound having an α-hydrogen of the formula (3). These compounds are subjected to a Mannich-type reaction to obtain 2-(2',2'-dimethoxy-1'-(4''-methoxyphenylamino)ethyl)cyclohexanone. The obtained compound has four kinds of enantiomers (Anti-1, Anti-2, (two) Syn), described below. The production ratio of the enantiomers may be controlled by selection of the kind of asymmetric catalyst particles.

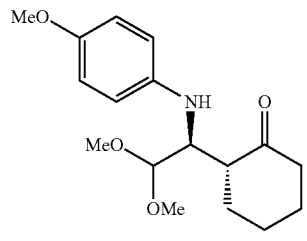

Anti-1 (1'S,2R enantiomer)

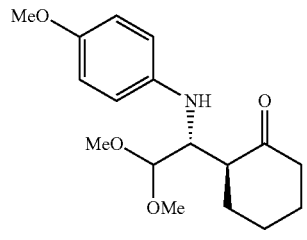

Anti-2 (1'R,2S enantiomer)

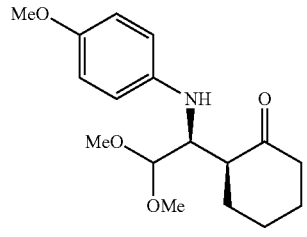

Syn-1 (1'S,2S enantiomer)

-continued

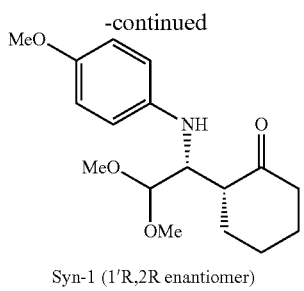

Syn-1 (1'R,2R enantiomer)

Among the enantiomers, (1'S,2S),2-(2',2'-dimethoxy-1'-(4"-methoxyphenylamino)ethyl)cyclohexanone is excellent industrially.

In the production method of the present invention, when the length, the diameter, or both of the column is extended, or the kind of a developing solvent is changed, the produced optically active β-aminocarbonyl compound can be further subjected to optical resolution in the column reactor. Specifically, when the length, the diameter, or both of the column is extended, the amount of catalyst to be used in optical resolution increases. For this reason, the frequency of occurrence of interaction between the product and the catalyst increases. Accordingly, the reaction product can be subjected to optical resolution, and the reaction ratio can be increased. When the solvent in which the compounds for a reaction are dissolved is changed into another developing solvent, the interactions between the developing solvent, the product, and the catalyst change. As a result, the retention times of the enantiomers differ. Therefore, the reaction product can be optically resolved.

(Asymmetric Catalyst Particles)

Examples of the asymmetric catalyst particles may include those obtained by suspension polymerization of a monomer composition containing a monomer having an asymmetric source (for example, 2,2'-bis(diphenylphosphino)-1,1'-binaphthyl (BINAP)) through a known process, and those in which an organic compound that becomes an asymmetric source (for example, 2,2'-bis(diphenylphosphino)-1,1'-binaphthyl (BINAP)) is hold in pores of a porous polymer or a porous ceramic. In particular, it is preferable that the asymmetric catalyst particles be resin particles that are prepared from a monomer composition containing a proline derivative monomer having an unsaturated bond and a radical polymerization initiator by general suspension polymerization, and act as a catalyst for an aldol reaction or a Mannich reaction. More preferably resin particles are prepared through a microchannel method in which the monomer composition is discharged into a continuous phase to form droplets of the monomer composition in the continuous phase, and the droplets are heated to radically polymerize the proline derivative monomer having an unsaturated bond. The microchannel method will be described below.

If necessary, the monomer composition may contain a monovalent or polyvalent unsaturated compound monomer. When the monomer composition contains a monovalent unsaturated compound monomer, there is an effect in which the viscosity of the monomer composition becomes low. When the monomer composition contains a polyvalent unsaturated compound monomer, there is an effect in which the hardness of the particles becomes high.

The proline derivative monomer having an unsaturated bond that constitutes the monomer composition has a proline structure (the following structures (A) to (D)) that acts as an asymmetric source even after radical polymerization, and constitutes a part of a resin matrix of the catalyst particles obtained by radical polymerization. Examples of the proline derivative monomer having an unsaturated bond may include as follows.

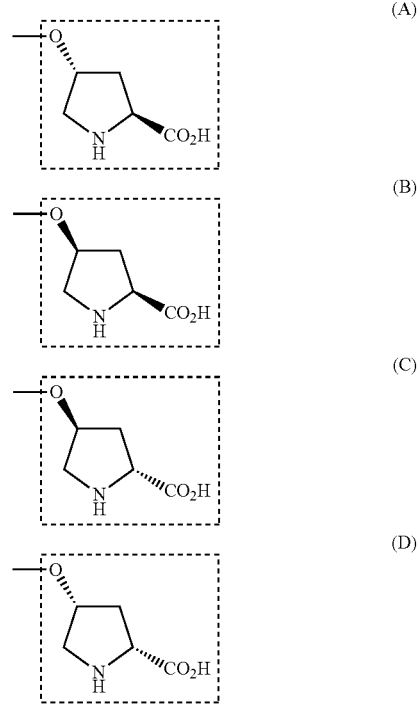

O-acryloyl-trans-4-hydroxy-L-proline
O-acryloyl-cis-4-hydroxy-L-proline
O-methacryloyl-trans-4-hydroxy-L-proline
O-methacryloyl-cis-4-hydroxy-L-proline
O-(2-methacryloyloxyethylsuccinoyl)-trans-4-hydroxy-L-proline
O-(2-methacryloyloxyethylsuccinoyl)-cis-4-hydroxy-L-proline
N-tert-butyloxycarbonyl-O-acryloyl-trans-4-hydroxy-L-proline
N-tert-butyloxycarbonyl-O-acryloyl-cis-4-hydroxy-L-proline
N-tert-butyloxycarbonyl-O-methacryloyl-trans-4-hydroxy-L-proline
N-tert-butyloxycarbonyl-O-methacryloyl-cis-4-hydroxy-L-proline
N-tert-butyloxycarbonyl-O-(2-methacryloyloxyethylsuccinoyl)-trans-4-hydroxy-L-proline
N-tert-butyloxycarbonyl-O-(2-methacryloyloxyethylsuccinoyl)-cis-4-hydroxy-L-proline
O-acryloyl-trans-4-hydroxy-D-proline
O-acryloyl-cis-4-hydroxy-D-proline
O-methacryloyl-trans-4-hydroxy-D-proline
O-methacryloyl-cis-4-hydroxy-D-proline
O-(2-methacryloyloxyethylsuccinoyl)-trans-4-hydroxy-D-proline
O-(2-methacryloyloxyethylsuccinoyl)-cis-4-hydroxy-D-proline
N-tert-butyloxycarbonyl-O-acryloyl-trans-4-hydroxy-D-proline
N-tert-butyloxycarbonyl-O-acryloyl-cis-4-hydroxy-D-proline N-tert-butyloxycarbonyl-O-methacryloyl-trans-4-hydroxy-D-proline N-tert-butyloxycarbonyl-O-methacryloyl-cis-4-hydroxy-D-proline N-tert-butyloxycarbonyl-O-(2-methacryloyloxyethylsuccinoyl)-trans-4-hydroxy-D-proline N-tert-butyloxycarbonyl-O-(2-methacryloyloxyethylsuccinoyl)-cis-4-hydroxy-D-proline N-tert-butyloxycarbonyl-O-(4-vinylbenzyl)-trans-4-hydroxy-L-proline N-tert-butyloxycarbonyl-O-(4-vinylbenzyl)-cis-4-hydroxy-L-proline N-tert-butyloxycarbonyl-O-(4-vinylbenzyl)-trans-4-hydroxy-D-proline N-tert-butyloxycarbonyl-O-(4-vinylbenzyl)-cis-4-hydroxy-D-proline Among them, from the viewpoints of obtention of starting material and ease of synthesis, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, N-tert-butyloxycarbonyl-O-(4-vinylbenzyl)-trans-4-hydroxy-L-proline, O-(2-methacryloyloxyethylsuccinoyl)-trans-4-hydroxy-L-proline, or the like, can be preferably used. These compounds can be prepared with reference to Patent Literature 1, J. Org. Chem., 2010, 75(5), pp. 1620 to 1629, Eur. J. Org. Chem., 2007, pp. 4688 to 4698, and the like.

In addition to the proline derivative monomer having an unsaturated bond, the monomer composition may contain a monovalent unsaturated compound monomer or a polyvalent unsaturated compound monomer, if necessary. The amount of monovalent unsaturated compound monomer or polyvalent unsaturated compound monomer to be mixed is preferably 100 to 10,000 parts by mass, and more preferably 300 to 1,900 parts by mass, relative to 100 parts by mass of the proline derivative monomer having an unsaturated bond.

Examples of the monovalent unsaturated compound monomer may include an olefin, a monovinyl aromatic compound, and a monofunctional (meth)acrylate (hereinafter, (meth)acrylate includes acrylate and methacrylate).

Examples of the olefin may include ethylene, propylene, butene, and a long-chain α-olefin. Examples of the monovinyl aromatic compound may include a n-alkyl-substituted monovinyl aromatic compound such as styrene, methylstyrene, and ethylstyrene, an α-alkyl-substituted monovinyl aromatic compound such as α-methylstyrene, a β-alkyl substituted styrene, an alkoxy-substituted styrene, an indene derivative, and an acenaphthylene derivative.

Examples of the monofunctional (meth)acrylate may include methyl (meth)acrylate, ethyl (meth)acrylate, n-propyl (meth)acrylate, i-propyl (meth)acrylate, n-butyl (meth)acrylate, i-butyl (meth)acrylate, tert-butyl (meth)acrylate, 2-methylbutyl (meth)acrylate, n-pentyl (meth)acrylate, n-hexyl (meth)acrylate, n-heptyl (meth)acrylate, 2-methylhexyl (meth)acrylate, 2-ethylhexyl (meth)acrylate, 2-butylhexyl (meth)acrylate, isooctyl (meth)acrylate, isopentyl (meth)acrylate, isononyl (meth)acrylate, isodecyl (meth) acrylate, cyclohexyl (meth)acrylate, benzyl (meth)acrylate, phenoxy (meth)acrylate, n-nonyl (meth)acrylate, n-decyl (meth)acrylate, lauryl (meth)acrylate, hexadecyl (meth)acrylate, and stearyl (meth)acrylate.

Examples of the polyvalent unsaturated compound monomer may include a polyvalent olefin, a polyvalent vinyl aromatic compound, and a polyfunctional (meth)acrylate.

Examples of the polyvalent olefin may include isoprene, 1,5-hexadiene, and 1,5-cyclooctadiene.

Examples of the polyvalent vinyl aromatic compound may include a divinyl aromatic compound such as m-divinylbenzene, p-divinylbenzene, 1,2-diisopropenylbenzene, 1,3-diisopropenylbenzene, 1,4-diisopropenylbenzene, 1,3-divinylnaphthalene, 1,8-divinylnaphthalene, 1,4-divinylnaphthalene, 1,5-divinylnaphthalene, 2,3-divinylnaphthalene, 2,7-divinylnaphthalene, 2,6-divinylnaphthalene, 4,4'-divinylbiphenyl, 4,3'-divinylbiphenyl, 4,2'-divinylbiphenyl, 3,2'-divinylbiphenyl, 3,3'-divinylbiphenyl, 2,2'-divinylbiphenyl, 2,4-divinylbiphenyl, 1,2-divinyl-3,4-dimethylbenzene, 1,3-divinyl-4,5,8-tributylnaphthalene, and 2,2'-divinyl-4-ethyl-4'-propynylbiphenyl, and a trivinyl aromatic compound such as 1,2,4-trivinylbenzene, 1,3,5-trivinylbenzene, 1,2,4-triisopropenylbenzene, 1,3,5-triisopropenylbenzene, 1,3,5-trivinylnaphthalene, and 3,5,4'-trivinylbiphenyl.

Examples of the polyfunctional (meth)acrylate may include a bifunctional (meth)acrylate such as bisphenol F-EO-modified di(meth)acrylate, bisphenol A-EO-modified di(meth)acrylate, polypropylene glycol di(meth)acrylate, polyethylene glycol (meth)acrylate, tricyclodecane dimethylol di(meth)acrylate, and dicyclopentadiene (meth)acrylate, a trifunctional (meth)acrylate such as trimethylolpropane tri(meth)acrylate, trimethylolpropane PO-modified (meth)acrylate, and isocyanuric acid EO-modified tri(meth) acrylate, and a tetra- or higher functional (meth)acrylate such as dipentaerythritol penta(meth)acrylate, dipentaerythritol hexa(meth)acrylate, pentaerythritol tetra(meth)acrylate, and ditrimethylolpropane tetra(meth)acrylate. In addition, a polyfunctional urethane (meth)acrylate can also be used. Specific examples thereof may include M1100, M1200, M1210, and M1600 (all available from TOAGOSEI CO., LTD.), and AH-600 and AT-600 (all available from KYOEISHA CHEMICAL CO., LTD.).

Among the monovalent unsaturated compound monomers or the polyvalent unsaturated compound monomers, divinylbenzene can be preferably used from the viewpoints of acid/base resistance, solvent resistance, particle hardness, and viscosity.

The radical polymerization initiator constituting the monomer composition is a compound that generates radicals by heating, and examples thereof may include an azo compound and an organic peroxide. Examples of the azo compound may include azobisalkanonitrile. Examples of the organic peroxide may include diacyl peroxide, peroxy dicarbonate, peroxy ester, peroxy ketal, dialkyl peroxide, and hydroperoxide. A "decomposition temperature" is an important indication for selection of the radical polymerization initiator from these compounds. As the decomposition temperature is lower, the low-temperature fast-curability of the monomer composition tends to be improved. For example, the decomposition temperature of the radical polymerization initiator herein represents a ten-hour half-life temperature.

Specific examples of the radical polymerization initiator used in the present invention may include azobisisobutyronitrile (decomposition temperature: 65° C.), diisobutyryl (decomposition temperature: 32.7° C.), 1,1,3,3-tetramethylbutylperoxy-2-ethylhexanoate (decomposition temperature: 65.3° C.), dilauroyl peroxide (decomposition temperature: 61.6° C.), di(3,5,5-trimethylhexanoyl) peroxide (decomposition temperature: 59.4° C.), tert-butyl peroxypivalate (decomposition temperature: 54.6° C.), tert-hexyl peroxypivalate (decomposition temperature: 53.2° C.), tert-butyl peroxyneoheptanoate (decomposition temperature: 50.6° C.), tert-butyl peroxyneodecanoate (decomposition temperature: 40.7° C.), tert-hexyl peroxyneodecanoate (decomposition temperature: 44.5° C.), di(2-ethylhexyl) peroxydicarbonate (decomposition temperature: 43.6° C.), di(4- tert-butylcyclohexyl) peroxydicarbonate (decomposition temperature: 40.8° C.), 1,1,3,3-tetramethylbutyl peroxyneodecanoate (decomposition temperature: 40.7° C.), di-sec-butyl peroxydicarbonate (decomposition temperature: 40.5° C.), di-n-propyl peroxydicarbonate (decomposition temperature: 40.3° C.), cumyl peroxyneodecanoate (decomposition temperature: 36.5° C.), di(4-methylbenzoyl) peroxide (decomposition temperature: 70.6° C.), di(3-methylbenzoyl) peroxide (decomposition temperature: 73.1° C.), dibenzoyl peroxide (decomposition temperature: 73.6° C.), 1,1-di(tert-butylperoxy)-2-methyl cyclohexane (decomposition temperature: 83.2° C.), 1,1-di(tert-hexylperoxy)cyclohexane (decomposition temperature: 87.1° C.), 1,1-di(tert-butylperoxy) cyclohexane (decomposition temperature: 90.7° C.), tert-hexyl peroxybenzoate (decomposition temperature: 99.4° C.), tert-butyl peroxybenzoate (decomposition temperature: 104.7° C.), methyl ethyl ketone peroxide (decomposition temperature: 15 to 35° C.) cyclohexanone peroxide, methyl cyclohexanone peroxide, tert-butyl hydroperoxide, tert-amyl hydroperoxide (decomposition temperature: 258° C.), tert-hexyl hydroperoxide (decomposition temperature: 116.4° C.), tert-octyl hydroperoxide (decomposition temperature: 150° C.), 2,5-dimethyl-2,5-dihydroperoxyhexane (decomposition temperature: 118° C.), cumene hydroperoxide (decomposition temperature: 157.9° C.), diisopropylbenzene monohydroperoxide, diisopropylbenzene dihydroperoxide (decomposition temperature: unknown), and para-menthane hydroperoxide (decomposition temperature: 128.0° C.). Two kinds or more thereof may be used in combination. The use of a high-decomposition temperature peroxide having a phenyl ring can improve the cohesive force of polymer to be produced.

In order to sufficiently achieve curing and avoid a decrease in polymerization degree to prevent a decrease in mechanical strength, the content of the radical polymerization initiator in the monomer composition is preferably 1 to 40 parts by mass, and more preferably 1 to 20 parts by mass, relative to the total amount of the proline derivative monomer having an unsaturated bond, and the monovalent unsaturated compound monomer, and the polyvalent unsaturated compound monomer to be mixed, if necessary, of 100 parts by mass.

In the monomer composition, a non-polymerizable polymer, an organic filler, an inorganic filler, a pigment, or the like may be mixed, if necessary.

(Microchannel Method)

As described above, it is preferable that the asymmetric catalyst particles be resin particles that are prepared through a microchannel method in which the monomer composition is discharged into a continuous phase to form droplets of the monomer composition in the continuous phase, and the droplets are heated to radically polymerize the proline derivative monomer having an unsaturated bond. This microchannel method includes the following steps (A) and (B). Hereinafter, each step will be described.

<Step (A)>

The monomer composition containing the proline derivative monomer having an unsaturated bond and the radical polymerization initiator is discharged from a microchannel into a continuous phase, to form droplets of the monomer composition in the continuous phase. This state is usually liquid/liquid emulsion. In order to discharge the monomer composition from the microchannel into the continuous phase, a known microreactor equipped with a microchannel (see Japanese Patent Nos. 2975943, 2981547, and 3616909) can be used. A commercially available microreactor can also be used. A microchannel applicable to the microreactor is not particularly limited. For example, a microsyringe, a microchannel chip in which a groove is formed on a glass substrate through etching, or the like can be used.

When a groove width, a groove depth, a groove length, a material of groove inner wall, and a discharge pressure of the microchannel, the kind of dispersion medium constituting the continuous phase, a dispersant, and the like are appropriately selected, the size of droplets of the monomer composition can be controlled. The size of the droplets is usually 1 to 100 μm. This size is the size of final asymmetric catalyst particles.

The continuous phase functions as the dispersion medium of droplets of the monomer composition, and is usually a solution in which a dispersant is dissolved in water such as ion-exchanged water. The dispersant can be appropriately selected from known cationic, anionic, nonioic, and amphoteric surfactants depending on the kinds of components of the monomer composition and the diameter of the droplets.

Examples of the anionic surfactant may include soap (fatty acid sodium), a monoalkylsulfate salt, an alkylpolyoxyethylene sulfate salt, an alkylbenzene sulfonate salt, and a monoalkyl phosphate salt. Examples of the cationic surfactant may include an alkyltrimethylammonium salt, a dialkyldimethylammonium salt, and an alkylbenzyldimethylammonium salt. Examples of the amphoteric surfactant may include alkyl dimethylamine oxide, and alkyl carboxybetaine. Examples of the nonionic surfactant may include a polyoxyethylene alkyl ether, a fatty acid sorbitan ester, alkylpolyglucoside, fatty acid diethanolamide, and an alkyl monoglyceryl ether.

The content of the surfactant in the continuous phase is generally 0.01 to 10% by weight, and preferably 0.05 to 5% by weight.

In order to stabilize the dispersion state of the droplets of the monomer composition and the asymmetric catalyst particles as a polymer of the monomeric composition, a stabilizing agent may be added to the continuous phase, if necessary. Examples of the stabilizing agent may include a water-soluble polymer such as polyvinyl alcohol, polyvinyl pyrrolidone, carboxymethyl cellulose, hydroxymethyl cellulose, starch, and gelatin, and a water-insoluble inorganic salt such as tricalcium phosphate.

The continuous phase may further contain a known additive such as a chelating agent (for example, glycine, alanine, and sodium ethylenediaminetetracetate), a pH buffer (for example, sodium tripolyphosphate, and potassium tetrapolyphosphate), a sensitizer, and a viscosity modifier.

<Step (B)>

Subsequently, the droplets of the monomer composition in the continuous phase are heated to radically polymerize the proline derivative monomer having an unsaturated bond. The droplets of the monomer composition may be heated by irradiation with microwave. When the output of microwave irradiation energy is changed, the heating temperature of droplets of the monomer composition can be controlled. Further, the level of mechanical properties of the asymmetric catalyst particles can be controlled. This is because occurrence of polymerization and depolymerization is recognized during heating by irradiation with microwave. The polymerization is likely to occur during an increase in heating temperature as compared with the depolymerization, and the mechanical properties, for example, the compressive strength (hardness of particles) of the polymer can be changed (i.e., controlled) without change of mixing composition of the monomer composition. As a microwave irradiation device, a commercially available device can be used.

Since the asymmetric catalyst particles obtained through the microchannel method are usually suspended in the continuous phase, the particles can be isolated by filtration, centrifugation, or the like. The average particle diameter, the 50% particle diameter, and the standard deviation of the asymmetric catalyst particles can be measured by a commercially available particle diameter measurement device. From the viewpoints of the effects of the present invention, it is preferable that the average particle diameter be 0.5 to 50 µm, the 50% particle diameter be 0.5 to 50 µm, the standard deviation be $5 \times 10^{-4}$ to 10 µm, and a CV value (=standard deviation/average particle diameter×100) be 0.1 to 20%.

<Column Reactor>

As described above, the column reactor is a column for a column reactor that is charged with the asymmetric catalyst particles. In a column reactor particularly suitable for the "method of producing an optically active β-aminocarbonyl compound" of the present invention, resin particles that are prepared from the monomer composition containing the proline derivative monomer having an unsaturated bond and the radical polymerization initiator and act as a catalyst of reaction that proceeds in an enamine mechanism such as an aldol reaction and a Mannich reaction are used as asymmetric catalyst particles. In particular, resin particles that are prepared through the microchannel method in which the monomer composition is discharged into the continuous phase to form droplets of the monomer composition in the continuous phase, and the droplets are heated to radically polymerize the proline derivative monomer having an unsaturated bond are used as asymmetric catalyst particles. As the proline derivative monomer having an unsaturated bond, the proline derivative monomer described above can be used. In particular, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline can be preferably used. As described above, it is preferable that the monomer composition further contain a monovalent or polyvalent unsaturated compound monomer, and preferably divinylbenzene. This column reactor is one aspect of the present invention, and a method of producing the same is also one aspect of the present invention.

Specifically, the method of producing the column reactor is characterized in that the above-described column for a column reactor is charged with the resin particles that are prepared from the monomer composition containing the above-described proline derivative monomer having an unsaturated bond and the radical polymerization initiator and act as a catalyst of reaction that proceeds in an enamine mechanism as asymmetric catalyst particles. In particular, as the asymmetric catalyst particles, the resin particles that are prepared through the microchannel method in which the monomer composition is discharged into the continuous phase to form droplets of the monomer composition in the continuous phase, and the droplets are heated to radically polymerize the proline derivative monomer having an unsaturated bond are preferably used.

EXAMPLES

Hereinafter, the present invention will be described specifically by Examples.

Example 1

Preparation of Asymmetric Catalyst Particles by Microchannel Method

As a dispersion phase, a monomer composition containing 90 parts by mass of divinylbenzene, 10 parts by mass of N-tert-butyloxycarbonyl-O-(4-vinylbenzyl)-trans-4-hydroxy-L-proline synthesized with reference to Non-Patent Literature 1 and J. Org. Chem., 2010, 75(5), pp. 1620 to 1629, 1 part by mass of dilauroyl peroxide (PEROYL L, available from NOF CORPORATION), and 30 parts by mass of iso-octane was prepared. As a continuous phase, an aqueous solution (continuous phase liquid) in which a surfactant (SSL, available from Kao Corporation) was dissolved in ion-exchanged water at a concentration of 1% by mass was prepared.

The prepared dispersion phase and continuous phase were set in a microreactor (manufactured by Eco Project Technologies Co., Ltd.) equipped with a microchannel (width: 5 µm, depth: 1 µm, length: 100 µm). The dispersion phase was extruded in the continuous phase to form droplets of the monomer composition having an average particle diameter of 3 µm. While the resulting mixture was mixed, ion-exchanged water and a surfactant (SSL, available from Kao Corporation) were added to prepare a slurry in which the concentration of droplets of the monomer composition was 4% by mass and the concentration of the surfactant was 1% by mass.

The resulting slurry was heated and stirred at 90 to 100° C. for 7 hours, collected by filtration through a filter, and dried under vacuum to obtain asymmetric catalyst particles in which polymerization and deprotection were completed. The particle diameter of the asymmetric catalyst particles was measured by a particle diameter measurement device (SD-2000, manufactured by SYSMEX CORPORATION). The average particle diameter was 2.881 µm, the 50% diameter was 2.883 µm, the standard deviation was 0.316 µm, and the CV value was 10.9.

(Production of Column Reactor)

The resulting asymmetric catalyst particles were added to ethanol at a concentration of 33.3% by weight, and the mixture was dispersed by ultrasonic to obtain a dispersion. The dispersion was placed in a stainless steel column (outer diameter: ¼ inches, inner diameter: 4.6 mm, length: 150 mm, Cat-No. 6010-11053, manufactured by GL Sciences Inc.) at a flow rate of 1.0 mL/min to obtain a column reactor for preparing an optically active β-aminocarbonyl compound. At this time, a pressure of up to 25.7 MPa was applied.

(Preparation of Optically Active β-Aminocarbonyl Compound)

The obtained column reactor was replaced with a mobile phase (hexane: cyclohexanone: triethylamine=89.85% by mass: 10% by mass: 0.15% by mass), injected with a mixture that had been stirred (mixture including 56% by mass of ethanol solution of dimethoxyacetaldehyde prepared at a concentration of 60% by mass and 44% by mass of p-anisidine), and developed at a flow rate of 0.1 mL/min. A reaction liquid discharged from the column reactor was analyzed by HPLC (LC-20A, manufactured by SHIMADZU CORPORATION (column: CHIRALPAK AS-H (manufactured by DAICEL CORPORATION), mobile phase: hexane-isopropyl alcohol mixed solvent (90% by volume:10% by volume). The resulting compound was identified by $^1$H-NMR and MS to be (1'S,2S),2-(2',2'-dimethoxy-1'-(4"-methoxyphenylamino)ethyl)cyclohexanone. The enantiomeric excess thereof was 91% e.e.

Example 2

(1'S,2S),2-(2',2'-dimethoxy-1'-(4"-methoxyphenylamino) ethyl)cyclohexanone was obtained in the same manner as in Example 1 except that 10 parts by mass of N-tert-butyloxycarbonyl-O-(2-methacryloxyethylsuccinoyl)-trans-4-hydroxy-L-proline was used instead of 10 parts by mass of N-tert-butyloxycarbonyl-O-(4-vinylbenzyl)-trans-4-hydroxy-L-proline in Example 1. The enantiomeric excess thereof was 74% e.e.

Example 3

(1'S,2S),2-(2',2'-dimethoxy-1'-(4"-methoxyphenylamino)ethyl)cyclohexanone was obtained in the same manner as in Example 1 except that 10 parts by mass of N-tert-butyloxycarbonyl-O-(2-methacryloxyethylsuccinoyl)-cis-4-hydroxy-L-proline was used instead of 10 parts by mass of N-tert-butyloxycarbonyl-O-(4-vinylbenzyl)-trans-4-hydroxy-L-proline in Example 1. The enantiomeric excess thereof was 7796e.e.

Example 4

(1'S,2S),2-(2',2'-dimethoxy-1'-(4"-methoxyphenylamino)ethyl)cycloheptanone was obtained in the same manner as in Example 1 except that cycloheptanone was used instead of cyclohexanone in Example 1. The enantiomeric excess thereof was 86% e.e.

Comparative Example 1

The same operation as in Example 1 except that 10 parts by mass of styrene was used instead of 10 parts by mass of N-tert-butyloxycarbonyl-O-(4-vinylbenzyl)-trans-4-hydroxy-L-proline in Example 1 was repeated. (1'S,2S),2-(2',2'-dimethoxy-1'-(4"-methoxyphenylamino)ethyl)cyclohexanone was not detected.

INDUSTRIAL APPLICABILITY

According to the method of producing an optically active β-aminocarbonyl compound of the present invention, an optically active β-aminocarbonyl compound can be produced using asymmetric catalyst particles so that an organic synthesis based on an asymmetric Mannich-type reaction can be easily performed without considering the reaction scale and the reaction product can be separated from the catalyst without a complex separating operation.

What is claimed is:

1. A column reactor in which a column for a column reactor is charged with asymmetric catalyst particles, wherein
the asymmetric catalyst particles are resin particles that are prepared from a monomer composition containing a proline derivative monomer having an unsaturated bond and a radical polymerization initiator, and that act as a catalyst for an asymmetric Mannich-type reaction, and
the asymmetric catalyst particles have a particle diameter of 1 to 10 μm, which are prepared through a microchannel method in which the monomer composition is discharged into a continuous phase to form droplets of the monomer composition in the continuous phase, and the droplets are heated to radically polymerize the proline derivative monomer having an unsaturated bond.

2. The column reactor according to claim 1, wherein the proline derivative monomer having an unsaturated bond is one selected from the group consisting of O-acryloyl-trans-4-hydroxy-L-proline, O-acryloyl-cis-4-hydroxy-L-proline, O-methacryloyl-trans-4-hydroxy-L-proline, O-methacryloyl-cis-4-hydroxy-L-proline, O-(2-methacryloyloxyethylsuccinoyl)-trans-4-hydroxy-L-proline, O-(2-methacryloyloxyethylsuccinoyl)-cis-4-hydroxy-L-proline, N-tert-butyloxycarbonyl-O-acryloyl-trans-4-hydroxy-L-proline, N-tert-butyloxycarbonyl-O-acryloyl-cis-4-hydroxy-L-proline, N-tert-butyloxycarbonyl-O-methacryloyl-trans-4-hydroxy-L-proline, N-tert-butyloxycarbonyl-O-methacryloyl-cis-4-hydroxy-L-proline, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-L-proline, O-acryloyl-trans-4-hydroxy-D-proline, O-acryloyl-cis-4-hydroxy-D-proline, O-methacryloyl-trans-4-hydroxy-D-proline, O-methacryloyl-cis-4-hydroxy-D-proline, O-(2-methacryloyloxyethylsuccinoyl)-trans-4-hydroxy-D-proline, O-(2-methacryloyloxyethylsuccinoyl)-cis-4-hydroxy-D-proline, N-tert-butyloxycarbonyl-O-acryloyl-trans-4-hydroxy-D-proline, N-tert-butyloxycarbonyl-O-acryloyl-cis-4-hydroxy-D-proline, N-tert-butyloxycarbonyl-O-methacryloyl-trans-4-hydroxy-D-proline, N-tert-butyloxycarbonyl-O-methacryloyl-cis-4-hydroxy-D-proline, N-tert-butyloxycarbonyl-O-(2-methacryloyloxyethylsuccinoyl)-trans-4-hydroxy-D-proline, N-tert-butyloxycarbonyl-O-(2-methacryloyloxyethylsuccinoyl)-cis-4-hydroxy-D-proline, N-tert-butyloxycarbonyl-O-(4-vinylbenzyl)-trans-4-hydroxy-L-proline, N-tert-butyloxycarbonyl-O-(4-vinylbenzyl)-cis-4-hydroxy-L-proline, N-tert-butyloxycarbonyl-O-(4-vinylbenzyl)-trans-4-hydroxy-D-proline, and N-tert-butyloxycarbonyl-O-(4-vinylbenzyl)-cis-4-hydroxy-D-proline.

3. The column reactor according to claim 1, wherein the proline derivative monomer having an unsaturated bond is one selected from the group consisting of N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, and N-tert-butyloxycarbonyl-O-(4-vinylbenzyl)-trans-4-hydroxy-L-proline.

4. The column reactor according to claim 1, wherein the monomer composition further contains any of a monovalent unsaturated compound monomer and a polyvalent unsaturated compound monomer.

5. The column reactor according to claim 1, wherein the monomer composition further contains divinylbenzene as a polyvalent unsaturated compound monomer.

6. A column reactor in which a column for a column reactor is charged with asymmetric catalyst particles, wherein
the asymmetric catalyst particles are resin particles having a particle diameter of 1 to 10 μm that are prepared by discharging a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a proline derivative monomer having an unsaturated bond, and a radical polymerization initiator into a continuous phase to form droplets of the monomer composition in the continuous phase, and heating the droplets to radically polymerize the proline derivative monomer having an unsaturated bond, and that act as a catalyst for the asymmetric Mannich-type reaction.

7. A method of producing an optically active β-aminocarbonyl compound by an asymmetric Mannich-type reaction using a column reactor of claim 1 in which a column is charged with asymmetric catalyst particles having a particle diameter of 1 to 10 μm, wherein
the method comprises introducing compounds for a Mannich-type reaction into the column reactor to bring the compounds into contact with the asymmetric catalyst particles, to thereby convert the compounds for a Mannich-type reaction to an optically active β-aminocarbonyl compound.

8. The method of producing an optically active β-aminocarbonyl compound according to claim 7, wherein the proline derivative monomer having an unsaturated bond is one selected from the group consisting of O-acryloyl-trans-4-hydroxy-L-proline, O-acryloyl-cis-4-hydroxy-L-proline, O-methacryloyl-trans-4-hydroxy-L-proline, O-methacryloyl-cis-4-hydroxy-L-proline, O-(2-methacryloyloxyethylsuccinoyl)-trans-4-hydroxy-L-proline, O-(2-methacryloyloxyethylsuccinoyl)-cis-4-hydroxy-L-proline, N-tert-butyloxycarbonyl-O-acryloyl-trans-4-hydroxy-L-proline, N-tert-butyloxycarbonyl-O-acryloyl-cis-4-hydroxy-L-proline, N-tert-butyloxycarbonyl-O-methacryloyl-trans-4-hydroxy-L-proline, N-tert-butyloxycarbonyl-O-methacryloyl-cis-4-hydroxy-L-proline, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-L-proline, O-acryloyl-trans-4-hydroxy-D-proline, O-acryloyl-cis-4-hydroxy-D-proline, O-methacryloyl-trans-4-hydroxy-D-proline, O-methacryloyl-cis-4-hydroxy-D-proline, O-(2-methacryloyloxyethylsuccinoyl)-trans-4-hydroxy-D-proline, O-(2-methacryloyloxyethylsuccinoyl)-cis-4-hydroxy-D-proline, N-tert-butyloxycarbonyl-O-acryloyl-trans-4-hydroxy-D-proline, N-tert-butyloxycarbonyl-O-acryloyl-cis-4-hydroxy-D-proline, N-tert-butyloxycarbonyl-O-methacryloyl-trans-4-hydroxy-D-proline, N-tert-butyloxycarbonyl-O-methacryloyl-cis-4-hydroxy-D-proline, N-tert-butyloxycarbonyl-O-(2-methacryloyloxyethylsuccinoyl)-trans-4-hydroxy-D-proline, N-tert-butyloxycarbonyl-O-(2-methacryloyloxyethylsuccinoyl)-cis-4-hydroxy-D-proline, N-tert-butyloxycarbonyl-O-(4-vinylbenzyl)-trans-4-hydroxy-L-proline, N-tert-butyloxycarbonyl-O-(4-vinylbenzyl)-cis-4-hydroxy-L-proline, N-tert-butyloxycarbonyl-O-(4-vinylbenzyl)-trans-4-hydroxy-D-proline, and N-tert-butyloxycarbonyl-O-(4-vinylbenzyl)-cis-4-hydroxy-D-proline.

9. The method of producing an optically active β-aminocarbonyl compound according to claim 7, wherein the proline derivative monomer having an unsaturated bond is one selected from the group consisting of N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, and N-tert-butyloxycarbonyl-O-(4-vinylbenzyl)-trans-4-hydroxy-L-proline.

10. The method of producing an optically active β-aminocarbonyl compound according to claim 7, wherein the monomer composition further contains any of a monovalent unsaturated compound monomer and a polyvalent unsaturated compound monomer.

11. The method of producing an optically active β-aminocarbonyl compound according to claim 7, wherein the monomer composition further contains divinylbenzene as a polyvalent unsaturated compound monomer.

12. The method of producing an optically active β-aminocarbonyl compound according to claim 7, wherein the compounds for a Mannich-type reaction include an amine compound represented by the formula (1), an aldehyde compound that reacts with the amine compound to produce an imine compound or an iminium cation compound and is represented by the formula (2), and a carbonyl compound having an α-hydrogen that is converted into an enol compound that reacts with the imine compound or the iminium cation compound and is represented by the formula (3),

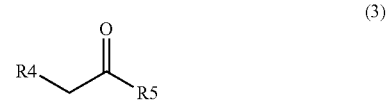

where in the formulas, R1, R2, and R3 are each independently a hydrogen atom, an aryl group, an aroyl group, a hetero-ring group, an alkyl group, an alkenyl group, or an alkynyl group, provided that R1 and R2 are not simultaneously hydrogen atoms; R4 and R5 are each independently a hydrogen atom, an alkyl group, an alkenyl group, or an alkynyl group; and R4 and R5 may be bonded together to form a ring.

13. The method of producing an optically active β-aminocarbonyl compound according to claim 12, wherein in the column reactor, the amine compound of the formula (1) reacts with the aldehyde compound of the formula (2) to produce an imine compound or an iminium cation compound, and the carbonyl compound of the formula (3) is enolized and reacts with the imine compound or the iminium cation compound in the presence of the asymmetric catalyst particles, to thereby obtain the optically active β-aminocarbonyl compound.

14. The method of producing an optically active β-aminocarbonyl compound according to claim 7, wherein the amine compound of the formula (1) is p-anisidine, the aldehyde compound of the formula (2) is dimethoxyacetaldehyde, and the carbonyl compound having an α-hydrogen of the formula (3) is cyclohexanone.

15. The method of producing an optically active β-aminocarbonyl compound according to claim 14, wherein the optically active β-aminocarbonyl compound is (1'S,2S),2-(2',2'-dimethoxy-1'-(4"-methoxyphenylamino)ethyl)cyclohexanone.

16. The method of producing an optically active β-aminocarbonyl compound according to claim 7, wherein the optically active β-aminocarbonyl compound converted from the compounds for a Mannich-type reaction is further subjected to optical resolution in the column reactor.

17. A method of producing an optically active β-aminocarbonyl compound by an asymmetric Mannich-type reaction using a column reactor of claim 1 in which a column is charged with asymmetric catalyst particles having a particle diameter of 1 to 10 μm, wherein
the asymmetric catalyst particles are resin particles that are prepared from a monomer composition containing N-tert-butyloxycarbonyl-O-(2-methacryloyloxyethylsuccinoyl)-trans-4-hydroxy-L-proline, N-tert-butyloxycarbonyl-O -(2-methacryloyloxyethylsuccinoyl)-cis-4-hydroxy-D-proline, or N-tert-butyloxycarbonyl-O-(4-vinylbenzyl)-trans-4-hydroxy-L-proline as a monomer having an asymmetric source, and a radical polymerization initiator, and act as a catalyst for the asymmetric Mannich-type reaction, and the method comprises introducing compounds for a Mannich-type reaction into the column reactor to bring the compounds into contact with the asymmetric catalyst particles, to thereby convert the compounds for a Mannich-type reaction to an optically active β-aminocarbonyl compound.

18. A method of producing an optically active β-aminocarbonyl compound by an asymmetric Mannich-type reaction using a column reactor of claim 1 in which a column is charged with asymmetric catalyst particles having a particle diameter of 1 to 10 μm, wherein the asymmetric catalyst particles are resin particles that are prepared from a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a monomer having an asymmetric source, and a radical polymerization initiator, and that act as a catalyst for the asymmetric Mannich-type reaction, and the method comprises introducing p-anisidine, dimethoxyacetaldehyde, and cyclohexanone into the column reactor to bring them into contact with the asymmetric catalyst particles, to thereby obtain (1'S,2S),2-(2',2'-dimethoxy- 1'-(4"-methoxyphenylamino)ethyl)cyclohexanone as an optically active β-aminocarbonyl compound.

19. A method of producing an optically active β-aminocarbonyl compound by an asymmetric Mannich-type reaction using a column reactor of claim 1 in which a column is charged with asymmetric catalyst particles having a particle diameter of 1 to 10 μm, wherein the asymmetric catalyst particles are resin particles that are prepared from a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a monomer having an asymmetric source, and a radical polymerization initiator, and that act as a catalyst for the asymmetric Mannich-type reaction, and the method comprises introducing p-anisidine, dimethoxyacetaldehyde, and cyclohexanone into the column reactor to bring them into contact with the asymmetric catalyst particles to thereby obtain (1S,2S),2-(2',2'-dimethoxy-1'-(4"-methoxyphenylamino)ethyl)cyclohexanone as an optically active β-aminocarbonyl compound, and further performing optical resolution in the column reactor.

20. A method of producing an optically active β-aminocarbonyl compound by an asymmetric Mannich-type reaction using a column reactor of claim 1 in which a column is charged with asymmetric catalyst particles having a particle diameter of 1 to 10 μm, wherein the asymmetric catalyst particles are resin particles that are prepared through a microchannel method in which a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a monomer having an asymmetric source, and a radical polymerization initiator is discharged into a continuous phase to form droplets of the monomer composition in the continuous phase, and the droplets are heated to radically polymerize the proline derivative monomer having an unsaturated bond, and that act as a catalyst for the asymmetric Mannich-type reaction, and the method comprises introducing p-anisidine, dimethoxyacetaldehyde, and cyclohexanone into the column reactor to bring them into contact with the asymmetric catalyst particles to thereby obtain (1'S,2S),2-(2',2'-dimethoxy-1'-(4"-methoxyphenylamino)ethyl)cyclohexanone as an optically active β-aminocarbonyl compound, and further performing optical resolution in the column reactor.

21. A method of producing a column reactor of claim 1, comprising charging a column for a column reactor with asymmetric catalyst particles having a particle diameter of 1 to 10 μm, wherein the asymmetric catalyst particles are resin particles that are prepared from a monomer composition containing a proline derivative monomer having an unsaturated bond and a radical polymerization initiator via a microchannel method in which the monomer composition is discharged into a continuous phase to form droplets of the monomer composition in the continuous phase, and the droplets are heated to radically polymerize the proline derivative monomer having an unsaturated bond, and that act as a catalyst for an asymmetric Mannich-type reaction.

22. A method of producing a column reactor of claim 1, comprising charging a column for a column reactor with asymmetric catalyst particles having a particle diameter of 1 to 10 μm, wherein the asymmetric catalyst particles are resin particles that are prepared by discharging a monomer composition containing N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline as a proline derivative monomer having an unsaturated bond, and a radical polymerization initiator into a continuous phase to form droplets of the monomer composition in the continuous phase, and heating the droplets to radically polymerize the proline derivative monomer having an unsaturated bond, and that act as a catalyst for the asymmetric Mannich-type reaction.

\* \* \* \* \*